United States Patent [19]

Barton et al.

[11] Patent Number: 4,868,307

[45] Date of Patent: Sep. 19, 1989

[54] DERIVATIVES OF BICYCLIC AMINOCARBOXYLIC ACIDS

[75] Inventors: Derek Barton, College Station, Tex.; Pierre Potier, Paris, France; Yolande Hervé, Puteaux, France; Josiane Thierry, Gif-sur-Yvette, France

[73] Assignee: Hoechst Aktiengesellschaft, Frankfurt am Main, Fed. Rep. of Germany

[21] Appl. No.: 127,953

[22] Filed: Dec. 2, 1987

[30] Foreign Application Priority Data

Dec. 4, 1986 [DE] Fed. Rep. of Germany ....... 3641451

[51] Int. Cl.$^4$ ................. C07D 401/00; C07D 413/00; C07D 417/00
[52] U.S. Cl. .................................... 546/256; 546/272; 546/273
[58] Field of Search ........................ 546/272, 273, 256

[56] References Cited

U.S. PATENT DOCUMENTS

| | | | |
|---|---|---|---|
| 4,350,704 | 9/1982 | Hoefle et al. | 546/272 |
| 4,435,408 | 3/1984 | Nedelec et al. | 546/273 |
| 4,587,258 | 5/1986 | Gold et al. | 514/412 |

FOREIGN PATENT DOCUMENTS

| | | | |
|---|---|---|---|
| 0037231 | 10/1981 | European Pat. Off. | 546/272 |
| 0050800 | 5/1982 | European Pat. Off. | 546/272 |
| 0079022 | 5/1983 | European Pat. Off. | 546/272 |
| 0084164 | 7/1983 | European Pat. Off. | 546/272 |
| 0111873 | 6/1984 | European Pat. Off. | 546/272 |
| 82/8085 | 10/1983 | South Africa | 546/272 |
| 82/9523 | 10/1983 | South Africa | 546/272 |
| 83/9344 | 8/1984 | South Africa | 546/272 |

*Primary Examiner*—Mary C. Lee
*Assistant Examiner*—Robert C. Whittenbaugh
*Attorney, Agent, or Firm*—Finnegan, Henderson, Farabow, Garrett & Dunner

[57] ABSTRACT

Derivatives of bicyclic aminocarboxylic acids, a process and intermediates for their preparation, and their use.

The invention relates to compounds of the formula

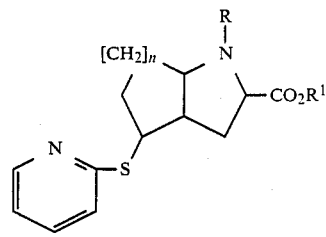

in which n is 1–3, R denotes acyl and $R^1$ denotes an esterifying group or another carboxyl-protecting group, a process and intermediates for their preparation, and their use.

3 Claims, No Drawings

DERIVATIVES OF BICYCLIC AMINOCARBOXYLIC ACIDS

DESCRIPTION

Derivatives of bicyclic aminocarboxylic acids, a process and intermediates for their preparations, and their use.

Acyl derivatives of octahydroindole-2-carboxylic acid, octahydrocyclopenta[b]pyrrole-2-carboxylic acid or decahydrocyclohepta[b]pyrrole-2-carboxylic acid are disclosed, for example, in EP-A-79,022, EP-A-50,800, EP-A-84,164, EP-A-111,873, EP-A-37,231, U.S. Pat. No. 4,350,704 or U.S. Pat. No. 4,587,258. Many of these compounds exhibit a notable biological activity. For example, they inhibit, highly effectively, the angiotensin-converting enzyme or are distinguished by a nootropic action.

Compounds of the formula IV

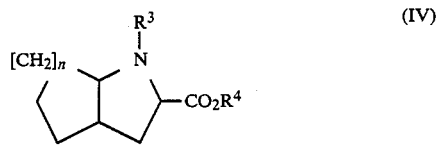

in which $R^3$ denotes hydrogen or an acyl radical, and $R^4$ denotes hydrogen, an ester group or another carboxyl-protecting group, play a key role in the synthesis of the acyl derivatives mentioned initially.

It is often advantageous for carbon atom C-2 in position 2 of the bicyclic ring system of these active compounds to have a certain absolute configuration, preferably the S configuration. Their synthesis therefore preferably starts from intermediates of the formula IV which already have this desired configuration at C-2.

In the preparation processes which are already known for compounds of the formula IV, a racemate resolution was unavoidable if compounds having a defined configuration at C-2 were desired.

It has now been found that thiohydroxamic acid derivatives, in particular N-hydroxy-2-thiopyridone derivatives, of appropriately substituted and configured aspartic acids can be converted into optically uniform compounds of the formula IV having the desired configuration at C-2 through cyclization and subsequent removal of a 2-thioxo-2H-[1]pyridyl radical, without a racemate resolution being necessary in any of the steps in this novel process.

Compounds of the formula I

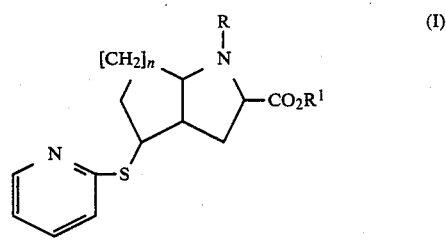

are important intermediates in this process.

The invention therefore relates to compounds of the formula I in which
N=1, 2 or 3,
R denotes $(C_1-C_{12})$-acyl and
$R^1$ denotes $(C_1-C_6)$-alkyl, $(C_3-C_7)$-cycloalkyl, $(C_7-C_{11})$-aralkyl or another carboxyl-protecting group, the hydrogen atoms on the bridgehead carbon atoms 3a and (5+n)a preferably having a cis-configuration.

The carbon atom in position 2 of the bicyclic ring system can have either the R or the S configuration; the S configuration is preferred.

R is preferably $(C_1-C_6)$-alkanoyl, $(C_6-C_{10})$-aryl-$(C_1-C_4)$-alkanoyl, $(C_6-C_{10})$-aroyl, $(C_1-C_6)$-alkoxycarbonyl or $(C_7-C_{11})$-aralkyloxycarbonyl, but in particular $(C_1-C_4)$-alkanoyl, such as acetyl or propionyl, or benzoyl or substituted benzoyl.

In addition, R, if not already covered by the definitions above, may represent a urethane type amine-protecting group which is conventional in peptide chemistry (cf., for example, Hubbuch, Kontakte Merck 3/79, 14–22). Urethane type protecting groups are, for example, Pyoc (4-pyridylmethoxycarbonyl), Fmoc (9-fluorenylmethyl-oxycarbonyl), Tcboc (2,2,2-trichloro-t-butyloxycarbonyl), Z (benzyloxycarbonyl), Boc (t-butoxycarbonyl), Ddz (α,α-dimethyl-3,5-dimethoxybenzyloxycarbonyl), Bpoc (1-(4-biphenylyl)-1-methylethoxycarbonyl), Adoc (1-adamantyloxycarbonyl), Msc (methyl-sulfonyl-ethyloxycarbonyl), Moc (4-methoxybenzyloxycarbonyl), Z(NO_2) (4-nitrobenzyloxycarbonyl), Z(Hal_n) (halogenosubstituted benzyloxycarbonyl), Dobz (4-dihydroxybornylbenzyloxycarbonyl), Iboc (isobornylcarbonyl), Adpoc (1-(1-adamantyl)-1-methyl-ethoxycarbonyl), Mobt (1-methyl-cyclobutyloxycarbonyl) and 1,4-dimethylpyridyloxycarbonyl.

$R^1$ is preferably $(C_1-C_4)$-alkyl, such as, for example, methyl, ethyl, or tert.-butyl, or $(C_7-C_{11})$-aralkyl, such as, for example, benzyl.

In addition, $R^1$, if not already covered by the definitions above, may represent a carboxyl-protecting group which is conventional in peptide chemistry (cf., for example, the abovementioned article by Hubbuch). Carboxyl-protecting groups are, for example, the abovementioned alkyl radicals or benzyl. Furthermore, modified benzyl radicals, such as p-nitrobenzyl, p-methoxybenzyl, p-bromobenzyl, p-chlorobenzyl and radicals such as 4-picolyl or benzoylmethyl, are suitable. Above and below, alkyl is taken to mean straight-chain or branched alkyl. In a corresponding fashion, the same applies to radicals derived therefrom, such as, for example, alkanoyl and aralkyl. Lower alkyl preferably has up to 6 carbon atoms. $(C_8-C_{10})$-aryl is, for example, phenyl or naphthyl, phenyl is preferred. In a corresponding fashion, the same applies to radicals derived therefrom, such as, for example, aroyl and aralkyl.

The invention furthermore relates to a process for the preparation of compounds of the formula I, wherein a compound of the formula II

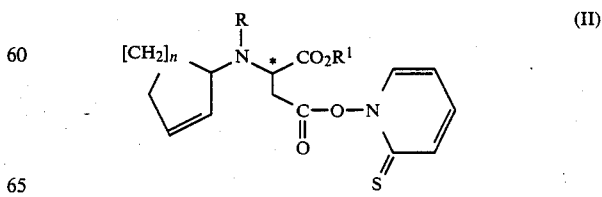

in which n, R and $R^1$ are as defined above, is subjected to free-radical decarboxylation.

Free-radical decarboxylation can be carried out, for example, by warming the compound to 40°–190° C., preferably 80°–130° C., in a suitable solvent, or alternatively without solvent, if appropriate in the presence of a free-radical initiator. Suitable solvents here are, in particular, aprotic solvents, such as benzene, toluene or xylene. Suitable initiators are, for example, organic peroxides, such as tert.-butyl peroxide, and substituted azoacetonitriles.

In addition, the free-radical decarboxylation can be carried out photolytically or radiolytically in a suitable dipolar aprotic solvent between −20° C. and the boiling point of the reaction mixture, preferably between 10° and 50° C. Photolytic decarboxylation is preferred. Suitable dipolar aprotic solvents are, for example, ethers, such as diethyl ether, tetrahydrofuran and dioxane.

The compounds of the formula II are prepared starting from cycloalkenyl bromides of the formula V

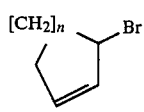
(V)

in which n is 1, 2 or 3. The latter compounds are reacted with aspartic acid derivatives of the formula VI

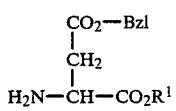
(VI)

in which $R^1$ is as defined above, but preferably denotes $(C_1-C_6)$-alkyl, such as tert. butyl, and which preferably have the L configuration, in the presence of a base, such as $K_2CO_3$, in a dipolar aprotic solvent, such as acetonitrile, between 0° C. and the boiling point of the reaction mixture, preferably at room temperature, to form compounds of the formula VII in which n and $R^1$ are as defined above.

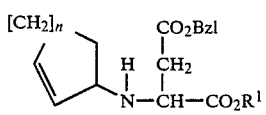
(VII)

The latter are acylated to form compounds of the formula VIII

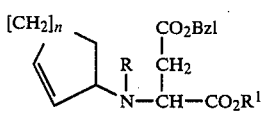
(VIII)

in which n, R and $R^1$ are as defined above. The acylation is expediently carried out in a dipolar aprotic solvent, such as acetone, in between −20° C. and the boiling point of the reaction mixture, preferably at room temperature, preferably in the presence of a base. Suitable acylating agents are, for example, chlorides of the formula RCl or anhydrides of the formula $R_2O$. Suitable bases are tertiary amines, such as triethylamine, and inorganic bases, such as $K_2CO_3$.

Hydrolysis of the diester VII using an alkali, preferably NaOH, in DMF at room temperature gives the compound of the formula IX

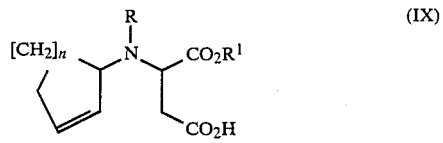
(IX)

in which n, R and $R^1$ are as defined above.

The latter compound is activated at −30° to 0° C. in a dipolar aprotic solvent, such as tetrahydrofuran, by adding a lower alkyl chloroformate, preferably isobutyl chloroformate, and a base such as n-methylmorpholine, giving intermediate compounds of the formula X

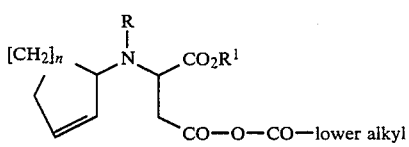

in which n, R and $R^1$ have the meaning above.

While maintaining the temperature, the alkali metal salt, preferably the sodium salt, of thiohydroxamic acids, preferably n-hydroxy-2H-pyridine-2-thione, is now added, forming the compound of the formula II.

Besides N-hydroxy-2H-pyridine-2-thione

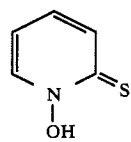

the following thiohydroxamic acids are also suitable, for example:

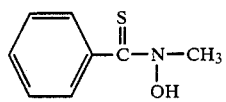

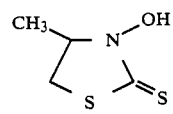

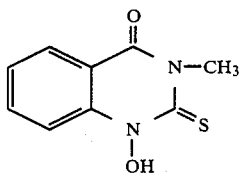

The invention also relates to compounds of the formula III

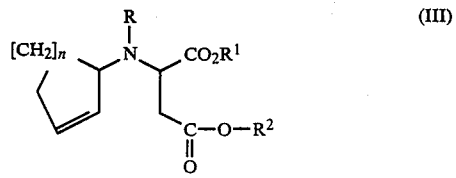

(III)

in which n, R and $R^1$ are as defined above, and $R^2$ denotes, in particular, 2-thioxo-2H-[1]pyridyl or ($C_1$-$C_6$)-alkoxycarbonyl, which are intermediates in the above-mentioned process.

In addition, the invention relates to the use of compounds of the formula I in a process for the preparation of a compound of the formula IV in which $R^3$ denotes hydrogen or is as defined for R, and $R^4$ denotes hydrogen or is as defined for $R^1$, through treatment of a compound of the formula I with Raney nickel in a suitable solvent, preferably a lower alcohol, water or dioxane, 1 or 2 of the radicals $R^3$ and/or $R^4$ which do not denote hydrogen subsequently being replaced, if appropriate, by hydrogen with the aid of acids and/or bases and/or hydrogenolytically, and a compound of the formula IV being converted, if desired, into an ester of the formula IV in which $R^4$ is as defined for R by esterification or transesterification. Bromine substituents on R=aroyl are replaced by hydrogen in this process. Lower alcohol is taken to mean an aliphatic alcohol having 1 to 4 carbon atoms; ethanol is preferred. The reaction is preferably carried out between $-20°$ C. and the boiling point of the reaction mixture, in particular between $10°$ and $40°$ C. Besides Raney nickel, other desulfurizing agents, such as, for example, nickel boride, can also be used.

The examples below serve to illustrate the invention without representing a limitation.

EXAMPLE 1

β-Benzyl α-tert.butyl N-(2-cyclohexen-1-yl)-L-aspartate

A solution of 3.22 g (20 mmol) of 3-bromocyclohexene in 20 ml of acetonitrile is introduced into a 250 ml flask containing 4.324 g (15.5 mmol) of β-benzyl α-tert.-butyl L-aspartate and 6.417 g (46.5 mmol) of potassium carbonate in 65 ml of anhydrous acetonitrile. The mixture is stirred vigorously at room temperature for 48 hours. The $K_2CO_3$ is filtered off and rinsed with plenty of acetonitrile. The solvent is evaporated at reduced pressure, and the amine is purified over silica gel (eluent: diethyl ether/hexane 1:1).

Yield: 5.02 g (89% of theory) of a slightly yellowish oil, $[\alpha]_D^{R.T.} = +5.1°$ (c=1, methanol).

IR: $\nu$=3320; 1735; 1500; 1455 cm$^{-1}$.

$^1$H NMR: δ[ppm]= 1.49 (9H, S, OtBu); 1.24–2.12 (yH, m, —(CH$_2$)$_3$—+NH) 3.12 (1H, m, —CH—NH—); 2.63 (2H, d, J=6 Hz, —CH$_2$—COOBzl); 3.62 (1H, t, J=6 Hz, —CH t); 5.09 (2H, s, —CH$_2$—Ph); 5.6 (2H, m, —CH=CH—); 7.28 (5H, s, Ph).

Elemental analysis ($C_{21}H_{29}NO_4$:359): calculated: % C 70.17 H 8.13 O 17.80. found: % C 69.99 H 7.99 O 17.86.

Mass spectrum: m/e; 360 (M$^+$+1) 259 (M$^+$-COOtBu). (R.T. in the optical rotation value represents "room temperature").

EXAMPLE 2

β-Benzyl α-tert.butyl N-acetyl-N-(2-cyclohexen-1-yl)-L-aspartate 1.1 g (3.06 mmol) of the amine from Example 1 are dissolved in 12 ml of acetone, and 1.1 g (3.06 mmol) of potassium carbonate are added. 0.43 ml of acetyl chloride (2 equivalents) dissolved in 3 ml of ether is then added, and the mixture is stirred vigorously at room temperature for 2 days. The carbonate is filtered off and rinsed with plenty of acetone, and the solvent is evaporated at reduced pressure. The polar amide is purified over a silica gel column (eluent: diethyl ether/hexane 1:1, then 2:1).

Yield: 1.19 g (97% of theory) of a colorless oil;

$[\alpha]_D^{R.T.} = -44.4°$ (c=1, methanol)

IR: δ=1740; 1730; 1675; 1650; 1500 cm$^{-1}$.

$^1$H NMR: [ppm]= 1.41 (9H, s, OtBu); 1.85 (6H, m) 2.06 (3H, s, COCH$_3$); 3.62 (2H, m, —CH$_2$—COOBzl); 4.19 (1H, dd, J$_1$=9 Hz, J$_2$=3 Hz, CH$_2$) 4.35 (1H, m, —CH—N); 5.1 (2H, s, —CH$_2$—Ph); 5.82 (2H, m, —CH=CH—); 7.3 (5H, s, —Ph).

Elemental analysis ($C_{23}H_{31}O_5N$: 401): calculated: % C 68.80, H 7.78, 0 19.93. found: % C 68.71, H 7.85, O 19.95.

Mass spectrum m/e=401 (M$^+$); 358 (M$^+$-COCH$_3$).

EXAMPLE 3

α-Tert.butyl N-acetyl-N-(2-cyclohexen-1-yl)-L-aspartate 1.3 g (3.24 mmol) of the amide from Example 2 are dissolved in 5 ml of DMF and hydrolysed at room temperature for 2½ days using 2 ml (1.2 equivalents) of 2N sodium hydroxide solution. The solvent is evaporated, and the residue is dissolved in 2 ml of water. It should be ensured that the pH is alkaline. This aqueous phase is washed with ether in order to remove the benzyl alcohol, and then acidified to a pH of 4 using solid citric acid. The mixture is then extracted with ethyl acetate. The organic phase is washed with saturated aqueous NaCl solution, dried over Na$_2$SO$_4$, filtered and evaporated on a rotary evaporator. The acid thus obtained is purified over a silica gel column (40 g of SiO$_2$ 60–200 μm; eluent CH$_2$Cl$_2$/methanol 98:2).

Yield: 910 mg (90% of theory) of a foam, $[\alpha]_D^{R.T.} = -108.9°$ (c=1.94; methanol).

IR: $\nu$=3350; 1740; 1700 cm$^{-1}$.

$^1$H NMR: δ[ppm]= 1.42 (9H, s, OtBu); 1.92 (6H, m); 2.12 (3H, s, —COCH$_3$); 3.56 (2H, m, —CH$_2$—); 4.16 (1H, dd, J$_1$=9 Hz, J$_2$=3 Hz, —CH$_2$); 4.35 (1H, m, —CH—N—); 5.51–5,86 (2H, m, —CH=CH—).

Mass spectrum m/e: 311 (M$^+$); 212 (M$^+$-COOtBu); 268 M$^+$-43).

EXAMPLE 4

β-Benzyl α-tert.butyl N-(p-bromobenzoyl)-N-(2-cyclohexen-1-yl)-L-aspartate 2.5 g (6.9 mmol) of β-benzyl α-tert.butyl L-aspartate are added to a suspension of 3.86 g (28 mmol) of potassium carbonate in 32 ml of acetone, and the solution of 2.26 g (10.3 mmol) of p-bromobenzoyl chloride in 10 ml of ether is added. The mixture is then stirred vigorously at room temperature for 2 days, the carbonate is filtered off and rinsed with plenty of acetone, and the solvent is evaporated at reduced pressure. The oil which remains is purified over a silica gel column (eluent: diethyl ether/hexane 1:3).

Yield: 3.046 g (81% of theory); m.p.: 100°-101° C. (from diethyl ether/hexane); $[\alpha]_D^{R.T.} = -49.8°$ (c=1.8; methanol).

IR (Nujol): $\nu = 1730; 1635; 1590; 1420$ cm$^{-1}$.

$^1$H NMR (200 MHz): [ppm]= 1.45 (9H, s, OtBu); 1.32-2.15 (6H, m, —CH$_2$—); O 2.47 (1H, dt, J$_1$=3 Hz; J$_2$=12 Hz; —CH$_2$—); —C—R 3.73 (1H, m, 1H of CH$_2$); 4.23 (2H, m, —CH—N—CH); 5.13 (2H, m, —CH$_2$—ph); 5.7 (2H, m, —CH=CH—); 7.28 (9H, m, Ar).

Elemental analysis (C$_{28}$H$_{32}$NO$_5$Br: 542): calculated: % C 61.99, H 5.94, N 2.59, 0 14.74. found: % C 61.87, H 5.78, N 2.46, O 14.47.

EXAMPLE 5

α-Tert.butyl N-(p-bromobenzoyl)-N-(2-cyclohexen-1-yl)-L-aspartate 1 g (1.8 mmol) of the amide from Example 4 is hydrolysed by adding 2 ml (1.1 equivalents) of 1N sodium hydroxide solution, the mixture is stirred at room temperature for 1 day, and the dioxane is then evaporated. The aqueous phase is washed with ether, its pH is adjusted to 4 using solid citric acid, and the mixture is then extracted with ethyl acetate.

The acid thus obtained is purified over a silica gel column (30 g of SiO$_2$ 70-200 μm; eluent) CH$_2$Cl$_2$/methanol 98:2)

Yield: 685 mg (84% of theory) of a foam.

IR: $\nu = 3450; 1730; 1680; 1585$; cm$^{-1}$.

$^1$H NMR: [ppm]= 1.47 (9H, s, OtBu); 1,3-2,62 (6H, m); 3.65 (2H, m, —CH$_2$—COOH); 4.22 (2H, m, —CH—N—CH); 5.84 (2H, m, —CH=CH—); 7.16 (2H, d, J=8 Hz); 7.47 (2H, d, J=8 Hz, Ar); 8.1 (1H, s, —COOH).

Microanalysis was carried out on the dicyclohexylamine salt, and similarly the melting point and optical rotation were determined for the dicyclohexylamine salt.

Elemental analysis: (C$_{33}$H$_{49}$N$_2$O$_5$Br: 633): calculated: % C 62.55, H 7.79, N 4.42, O 12.62. found: % C 62.32, H 7.68, N 4.25, O 12.47.

$[\alpha]_D^{R.T.} = -9.1°$ (c=0.76; methanol).

m.p.: 156°-157° C. [from ethyl acetate/petroleum ether].

EXAMPLE 6

Tert.-butyl 1-acetyl-4-(2'-pyridyl)-mercaptoperhydroindole-2-L-carboxylate 0.28 ml (2.5 mmol) of N-methylmorpholine and 0.36 ml (2.5 mmol) of isobutyl chloroformate are added while stirring to a solution of 776 mg (2.5 mmol) of the acid from Example 3 in 13 ml of THF under argon at −15° C. After an activation time of 5 minutes, 484 mg (1.3 equivalents) of the sodium salt of N-hydroxy-2H-pyridine-2-thione are added, and the mixture is stirred for 1.5 hours at −15° C. under argon while excluding light. The mixture is then diluted with 20 ml of THF and allowed to stand at room temperature for 2 hours. The THF is evaporated under reduced pressure, and the residue is purified over silica gel (eluent: diethyl ether/hexane 2:1, 3:1, then 4:1 and, as soon as the first diastereoisomer has been removed, diethyl ether must be used as the eluent).

| Balance: diastereomer 1 | 263 mg |
| Mixture of | |
| diastereomers 1 and 2 | 160 mg |
| Diastereomer 2 | 151 mg |
| Total yield | 574 mg (56% of theory) |

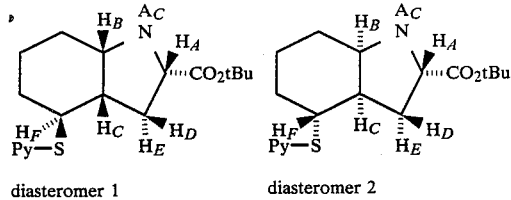

(Py = 2'-pyridyl; Ac = acetyl; tBu = tert.butyl)

The 160 mg of the diastereomeric mixture above were separated by means of preparative thin-layer chromatography (SiO$_2$; mobile phase: diethyl ether/hexane 1:1), a further 17 mg of diastereomer 1 and 125 mg of diastereomer 2 being obtained.

Diastereomer 1:

Pale yellow oil; $[\alpha]_D^{R.T.} = -67.9°$ (c=0.6; methanol).

IR: $\nu = 1740; 1720; 1640; 1585; 1560$ cm$^{-1}$.

$^1$H NMR (200 MHz): δ[ppm]= 1.53 (9H, s, OtBu); 2.18 (3H, s, —COOH$_3$); 1.43-2.35 (7H, m, —CH$_2$—); 2.5 (1H, m, H$_D$ or H$_E$, 2.72 (1H, m H$_C$); 4.15 (1H, m, H$_B$); 4.45 (1H, t, J=10 Hz, H$_F$); 4.58 (1H, m, H$_A$); 7.23-7.93 (3H, m, —S—Py); 8,8 (1H, m, —S—Py)

Mass spectrum: m/e=376 (M+), 320 (M+-=<), 276 (M+-COOtBu) 265 (M+—S—Py).

Diastereomer 2: m.p.: 163°-165° C. [from diethyl ether/hexane];

$[\alpha]_D^{R.T.} = +19.3°$ (c=0.7; methanol).

$^1$H NMR (400 MHz); δ[ppm]= 1.5 (9H, s, OtBu); 2.12 (3H, S, —COCH$_3$); 1.16-2.29 (7H, m); 2.39 (1H, m, H$_D$ or H$_E$); 2.63 (1H, m, H$_C$); 3.97 (1H, m, H$_B$); 4.26 (1H, t, J=9 Hz, H$_F$); 4.36 (1H, m, H$_A$); 6.88-7.58 (3H, m, S—Py); 8.38 (1H, m).

IR: $\nu = 1740; 1720; 1640; 1585; 1560$ cm$^{-1}$.

Mass spectrum: m/e=376 (M+), 320 (M+-=<), 276 (M+-COOtBu), 265 (M+—S—Py).

EXAMPLE 7

Tert.butyl 1-(p-bromobenzoyl)-4-[(2'-pyridyl)-mercapto]perhydroindole-2-L-carboxylate The title compound was prepared in a fashion analogous to Example 6 starting from 600 mg (1.3 mmol) of the acid from Example 5.

Separation by column chromatography (SiO$_2$, eluent diethyl ether/hexane 1:2, later 1:1) led to resolution of the diastereomers.

| Balance: diastereomer 1' | 205 mg |
| mixture of | |
| diastereomers 1' and 2' | 135 mg |
| diastereomer 2' | 125 mg |
| total yield | 465 mg (69% of theory) |

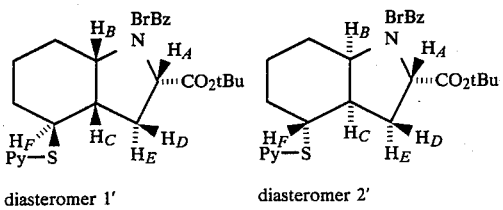

diastereomer 1'  diastereomer 2'

(Py = 2'-pyridyl; BrBz = p-bromobenzoyl; tBu = tert.butyl)

Diastereomer 1': m.p.: 164°–165° C. [from ethanol], $[\alpha]_D = -170.0°$ (c=1.09; methanol)

IR: $\nu = 1740; 1640; 1600; 1580; 1560; 1450;$ cm$^{-1}$.

$^1$H NMR (200 MHz): δ[ppm]= 1.48 (9H, m); 1.1–2.33 (7H, m, —CH$_2$); 2.48 (2H, m, H$_C$+H$_D$ or (H$_E$)); 3.76 (1H, m, H$_B$); 4.31 (1H, m, H$_F$)); 4.45 (1H, m, H$_A$)); 6.86–7.68 (8H, Ar); 8.36 (1H, m).

Elementary analysis (C$_{25}$H$_{29}$N$_2$O$_3$Br: 517): calculated: % C 58.01, H 5.64, N 5.44, O 9.27. found: % C 57.88, H 5.48, N 5.49, O 9.08.

Diastereomer 2':

foam; $[\alpha]_D^{R.T.} = +63.9°$ (c=0.8; methanol).

$^1$H NMR (400 MHz): δ[ppm]= 1.44 (9H, s, —OtBu); 0.8–1.91 (6H, m, —(CH$_2$)$_3$—); 2.09 (1H, dd, $J_{EA}=0$, $J_{ED}=13$ Hz, $J_{EC}=7$ Hz, H$_E$); 2.36 (1H, dt, $J_{DE}=J_{DC}=13$ Hz, $J_{DA}=10$ Hz, H$_D$); 2.83 (1H, m, H$_C$); 4.03 (1H, m, H$_B$); 4.27 (1H, m, H$_F$); 4.6 (1H, d, $J_{DA}=10$ Hz, H$_A$); 6.90–7.68 (7H, m); 8.32 (1H, m).

Mass spectrum: m/e: 515, 517, 518, (M+), 461 (M+=<) 317 (M+-COOtBu), 406 (M+—S—Py).

EXAMPLE 8

Tert.butyl cis,exo-N-benzoyl-perhydroindole-2-L-carboxylate 150 mg (0.29 mmol) of diastereomer 1' from Example 7 are dissolved in 2 ml of absolute ethanol and reduced overnight at room temperature using Raney nickel (®Prolabo, 50% shrink in water). The mixture is subsequently filtered, the catalyst is rinsed with plenty of an ethanol/water mixture, and the solvent is evaporated on a rotary evaporator.

Yield: 100 mg of crude product.

EXAMPLE 9

Cis,exo-N-benzoyl-perhydroindole-2-L-carboxylic acid

The crude product from Example 8 is hydrolyzed for one hour at room temperature in a mixture of 0.2 ml of a trifluoroacetic acid and 0.2 ml of CH$_2$Cl$_2$. The mixture is subsequently evaporated, and the oily residue (87 mg) is washed with pentane.

EXAMPLE 10

Ethyl cis,exo-N-benzoyl-perhydroindole-2-L-carboxylate

The acid from Example 9 is dissolved in 1.2 ml of DMF and neutralized using 52 mg (0.6 mmol) of NaHCO$_3$. A solution of 0.1 ml (1.25 mmol) of ethyl bromide in 1.2 ml of DMF is now added, and the mixture is stirred at room temperature for 24 hours. The DMF is evaporated under reduced pressure, and the residue is taken up in 1.5 ml of a 10% strength aqueous citric acid solution. The title compound is extracted with ethyl acetate and then purified by chromatography (preparative TLC, SiO$_2$; mobile phase: diethyl ether/hexane 1:1).

Yield 57 mg (65% of theory) of a colorless oil; $[\alpha]_D = -41.1°$ (c=0.48, methanol).

IR: $\nu = 1750; 1640; 1600; 1570$ cm$^{-1}$.

$^1$H NMR (400 MHz): δ[ppm]= 1.30 (3H, m, —CO—CH$_2$—CH$_3$); 0.85–1.94 (8H, m, —(CH$_2$)$_4$); 2.07 (1H, dt, $J_{ED}=J_{EC}=13$ Hz, $J_{EA}=8$ Hz, H$_E$); 2.23 (1H, m, H$_D$); 2.38 (1H, m, H$_C$); 3.57 (1H, m, H$_B$); 4.24 (2H, m, —CO—CH$_2$—CH$_3$); 4.62 (1H, dd, $J_{AE}=8$ Hz, $J_{AD}=6$ Hz, H$_A$); 7.31 (2.5H, Ar); 5.87 (2.5H, Ar). [numbering of the H atoms as for diastereomers 1' and 2']

Mass spectrum: m/e=301 (M+), 237 (M+-COOEt), 196 (M+—CO—Ph).

EXAMPLE 11

Ethyl cis,endo-N-benzoyl-perhydroindole-2-L-carboxylate

The procedure described above under Examples 8–10 is carried out using 120 mg (0.23 mmol) of diastereomer 2' from Example 7.

Yield: 46 mg (66% of theory) of white crystals;

m.p.: 111°–112° C. [from diethyl ether/pentane]; $[\alpha]_D^{R.T.} = -91.9°$ (c=0.47; methanol)

IR: $\nu = 1750; 1640; 1600; 1570$ cm$^{-1}$.

$^1$H NMR (400 MHz): δ[ppm]= 1.3 (3H, t, J=7 Hz, CH$_3$—); 0.83–1,78 (8H, m, —(CH$_2$—)$_4$); 1.87 (1H, dd, $J_{EA}=0$, $J_{EB}=13$ Hz, $J_{EC}=6,5$ Hz, H$_E$); 2.23 (1H, dt, $J_{DA}=10$ Hz, $J_{DE}=J_{DC}=13$ Hz, H$_D$); 2.67 (1H, m, H$_C$); 3.26 (1H, m, H$_B$); 4.22 (2H, q, J=7 Hz, —CH$_2$—CH$_3$); 4.69 (1H, d, $J_{AD}=10$ Hz, H$_A$); 7.37 (2.5H, m, Ar); 7.48 (2.5H, m, Ar). [numbering of the H atoms as for diastereomers 1' and 2']

Mass spectrum: m/e=301 (M+), 237 (M+-COOEt), 196 (M+-COPh).

EXAMPLE 12

Tert.butyl cis,exo-N-acetyl-perhydroindole-2-L-carboxylate 150 mg (0.4 mmol) of diastereomer 1 from Example 6 are dissolved in 3 ml of ethanol and reduced overnight while stirring at room temperature using a raney nickel. The nickel is filtered off and rinsed with a water/ethanol mixture, and the filtrate is evaporated in vacuo.

Crude yield: 130 mg

EXAMPLE 13

Cis,exo-perhydroindole-2-L-carboxylic acid hydrochloride

The crude product from Example 12 is refluxed for one hour with 4 ml of 6N hydrochloric acid. After evaporation in vacuo, the hydrochloride remains in the form of an oil.

EXAMPLE 14

Ethyl cis,exo-perhydroindole-2-L-carboxylate hydrochloride

Hydrogen chloride is passed into a solution of the hydrochloride from Example 13 in a 3 ml of absolute ethanol for 5 minutes at room temperature and for 10 minutes at 0° C. After evaporation of the ethanol, the residue remains as the hydrochloride of the ethyl ester (100 mg).

EXAMPLE 15

Ethyl cis,exo-N-(p-bromobenzoyl)-perhydroindole-2-L-carboxylate

The ester hydrochloride from Example 14 is dissolved in a mixture of 3 ml of THF and 1 ml of $CH_2Cl_2$, and, at 0° C., 0.07 ml (0.5 mmol) of triethylamine is added. 151 mg (0.75 mmol) of p-bromobenzoic acid, 115 mg (0.75 mmol) of hydroxybenzotriazole and 155 mg (0.75 mmol) of dicyclohexylcarbodiimide are then added successively at 0° C., and the mixture is stirred vigorously at room temperature for 24 hours. The dicyclohexylurea is filtered off and rinsed with THF, and the solvent is evaporated from the filtrate.

The residue is dissolved in 5 ml of ethyl acetate, and the organic phase is washed successively with 0.1N aqueous $NaHCO_3$ solution, water, 0.5N hydrochloric acid, again with water and a saturated aqueous NaCl solution. The organic phase is then dried over $Na_2SO_4$, filtered and evaporated in vacuo. The derivative thus obtained is now purified by means of preparative thin-layer chromatography ($SiO_2$; eluent diethyl ether/hexane 1:1).

Yield: 62 mg (41% of theory) of a colorless oil;
$[\alpha]_D^{R.T.} = -39.1°$ (c=0.6; ethanol).
IR: $\nu = 1745$; 1635; 1595; 1490 $cm^{-1}$.
$^1H$ NMR (200 MHz): $\delta$[ppm]= 1.3 (3H, m, $CH_3$); 0.83-1.95 (8H, m, —$(CH_2)_4$—); 2.17 (1H, m, $H_E$); 2.37 (1H, dt, $J_{DC}=J_{DA}=8$ Hz, $J_{DE}=16$ Hz, $H_D$) 2.71 (1H, m, $H_C$); 3.6 (1H, m, $H_B$); 4.27 (2H, m, —$COOCH_2$—$CH_3$); 4.67 (1H, m, $H_A$); 7.37 (2H, d, J=9 Hz); 7.6 (2H, d, J=9 Hz). [numbering of the H atoms as for diastereomers 1 and 2]

Mass spectrum: m/e=320 (M+), 307 (M+-COOEt), 196 (M+-COAr).

EXAMPLE 16

Ethyl cis,endo-N-(p-bromobenzoyl)-perhydroindole-2-L-carboxylate

Starting from 120 mg (0.32 mmol) of diastereomer 2 from Example 6, 55 mg (45% of theory) of the title compound are obtained, in the form of an oil, analogously to Examples 12-15.

$[\alpha]_D^{R.T.} = -54.4°$ (c=1.1; ethanol).
IR: $\nu = 1745$; 1635; 1595; 1495; $cm^{-1}$.
$^1H$ NMR (200 MHz); $\delta$[ppm] 1.32 (3H, t, J=7 Hz, —$CH_3$); 0.83-1.8 (8H, m, —$(CH_2)_4$—); 1.88 (1H, dd, $J_{ED}=13$ Hz, $J_{EC}=6.5$ Hz, $H_E$); 2.37 (1H, dt, $J_{DE}=J_{DC}=13$ Hz; $J_{DA}=9$ Hz, $H_D$); 2.6 (1H, m, $H_C$); 3.87 (1H, ddd, $^JBH_1=16$ Hz, $^JBH_2=10.5$ Hz, $J_{BC}=5$ Hz)$H_B$); 4.2 (2H, q, J=7 Hz, —O—$CH_2$—$CH_3$); 4.68 (1H, d, J=9 Hz, $H_A$); 7.38 (2H, d, J=9 Hz); 7.55 (2H, d, J=9 Hz). [numbering of the H atoms as for diastereomers 1 and 2]

Mass spectrum: m/e=380 (M+), 307 (M+-COOEt), (M+-COAr).

EXAMPLE 17

Tert.butyl cis,exo-N-benzoyl-perhydroindole-2-L-carboxylate

The title compound is obtained starting from diastereomer 1' from Example 7 through treatment with Raney nickel in ethanol. Purification is effected by means of preparative thin-layer chromatography ($SiO_2$; mobile phase diethyl ether/hexane 1:1).

m.p.: 114°-115° C. [from ethanol];
$[\alpha]_D^{R.T.} = -44.2°$ (c=0.9; methanol).
IR: $\nu = 1740$; 1640; 1600; 1420 $cm^{-1}$.
$^1H$ NMR (200 MHz): $\delta$[ppm]= 1.58 (9H, m, OtBu); 0.96-1.96 (8H, m, —$(CH_2)$—)$_4$); 2.18 (2H, m, $H_D$, $H_E$); 2.43 (1H, m, $H_C$); 3.73 (1H, m, $H_8$); 4.7 (1H, m, $H_A$); 7.7 (5H, m, Ar). [numbering of the H atoms as for diastereomers 1' and 2']

Mass spectrum: m/e=329 (M+), 229 (M+-COOtBu), 224 (M+—CO—Ph).

EXAMPLE 18

Tert.butyl cis,endo-N-benzoyl-perhydroindole-2-L-carboxylate

The title compound is obtained starting from the diastereomer 2' from example 7 to treatment with Raney nickel in ethanol. Purification is effected by means of preparative thin-layer chromatography ($SiO_2$; mobile phase diethyl ether/hexane 1:1).

m.p.: 111°-112° C. [from ethanol];
$[\alpha]_D^{R.T.} = -96.6°$ (c=1.05; methanol).
IR: $\nu = 1740$; 1640; 1600; 1420 $cm^{-1}$.
$^1H$ NMR (400 MHz): $\delta$[ppm]= 1.5 (9H, s, OtBu); 0.82-1.7 (8H, m, —$(CH_2)_4$; 1.84 (1H, dd, $J_{EA}=0$, $J_{ED}=13$ Hz, $J_{EC}=6.5$ Hz, $H_E$); 2.31 (1H, dt, $J_{DA}=10$ Hz, $J_{DE}$-$J_{DC}=13$ Hz, $H_D$); 2.67 (1H, m, $H_C$); 3.86 (1H, m, $H_B$); 4.56 (1H, d, J=10 Hz, $H_A$); 7.42 (5H, m, Ar). [numbering of the H atoms as for diastereomers 1' and 2'].

Elemental analysis ($C_{20}H_{27}NO_3$): calculated: % C 72.91, H 8.26, O 14.57. found: % C 72.83, H 8.38, O 14.81.

We claim:

1. A compound of the formula I

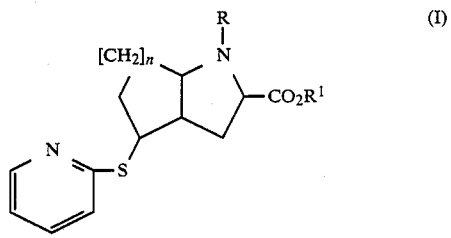

in which n=1, 2 or 3,

R is ($C_1$-$C_6$)-alkanoyl, ($C_6$-$C_{10}$)-aryl-($C_1$-$C_4$)-alkanoyl, ($C_6$-$C_{10}$)-aryl, ($C_1$-$C_6$)-alkoxycarbonyl, ($C_7$-$C_{11}$)-aralkyloxycarbonyl or, if not covered by the above definition, R is a urethane type protecting group selected from Pyoc, Fmoc, Tcboc, Z, Boc, Ddz, Bpoc, Adoc, Msc, Moc, Z($NO_2$), Z($Hal_n$), Dobz, Iboc, Adpoc, Mobt and 1,4-dimethylpyridyloxycarbonyl, and $R^1$ is ($C_1$-$C_6$)-alkyl, ($C_3$-$C_7$)-cycloalkyl, ($C_7$-$C_{11}$)-aralkyl, p-nitrobenzyl, p-methoxybenzyl, p-bromobenzyl, p-chlorobenzyl, 4-picolyl or benzoylmethyl.

2. A compound of the formula I as claimed in claim 1, in which the hydrogen atoms on the bridgehead carbon atoms 3a and (5+n)a have a cis configuration.

3. A compound of the formula I as claimed in claim 1, in which the carbon atom in position 2 has the S configuration.

* * * * *

UNITED STATES PATENT AND TRADEMARK OFFICE
CERTIFICATE OF CORRECTION

PATENT NO. : 4,868,307

DATED : September 19, 1989

INVENTOR(S) : Derek Barton et al.

It is certified that error appears in the above-identified patent and that said Letters Patent is hereby corrected as shown below:

Claim 1, column 12, line 51, change "aryl" to --aroyl--.

Signed and Sealed this

Thirtieth Day of July, 1991

Attest:

HARRY F. MANBECK, JR.

Attesting Officer

Commissioner of Patents and Trademarks